US00PP12904P2

(12) United States Plant Patent
Olesen et al.

(10) Patent No.: US PP12,904 P2
(45) Date of Patent: Sep. 3, 2002

(54) FLORIBUNDA ROSE PLANT NAMED 'POULBELLA'

(75) Inventors: L. Pernille Olesen; Mogens N. Olesen, both of Fredensborg (DK)

(73) Assignee: Poulsen Roser APS, Fredensborg (DK)

( * ) Notice: Subject to any disclaimer, the term of this patent is extended or adjusted under 35 U.S.C. 154(b) by 0 days.

(21) Appl. No.: 09/259,368

(22) Filed: Feb. 26, 1999

(51) Int. Cl.[7] ..... A01H 5/00
(52) U.S. Cl. ..... Plt./149
(58) Field of Search ..... Plt./141, 148, 149, Plt./150

(56) References Cited

PUBLICATIONS

UPOV–ROM, 2000/05, Plant Variety Database, GTI Jouve Retrieval Software, 3 citations for 'POULbella'.*
Copy of EU0309 granted Aug. 2, 1996 and QZ PBR 950439 filed Aug. 2, 1995.*
Copy of DK PBR 15773 filed Dec. 2, 1992 and grant #15773, granted Feb. 3, 1994.*
Copy of PL 0730, granted Aug. 31, 1995.*

* cited by examiner

*Primary Examiner*—Howard J. Locker

(57) ABSTRACT

A new garden rose plant which has abundant, hot pink flowers and attractive foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between an unnamed seedling and an unnamed seedling. The two parents were crossed in the summer of 1989 and the resulting seeds were planted in a controlled environment. The new variety is named 'POULbella'.

The new rose may be distinguished from its seed parent, an unnamed seedling, by the following combination of characteristics:

The unnamed seedling is a tall growing floribunda with bright pink, semi-double flowers. The unnamed seedling is an offspring of EGESKOV, a light pink floribunda and Dolly, a dark pink floribunda.

The new variety may be distinguished from its pollen parent, an unnamed seedling created by the same inventors, by the following combination of characteristics:

The pollen parent is a pink floribunda with double flowers and a low and compact habit. One of the parents of the seedling is Bella Rosa, a medium pink floribunda.

The objective of the hybridization of this rose variety for nursery and garden use was to create a new and distinct variety with unique qualities, such as:

1. Uniform and abundant double, hot pink flowers;
2. Vigorous, compact growth with shiny, dark green foliage;
3. Continual flowering; and
4. Good disease resistance.

This combination of qualities is not present in previously available commercial cultivars of this type and distinguish 'POULbella' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULbella' was selected by the inventors in the spring of 1989 as a single plant from the progeny of the aforementioned hybridization.

Asexual reproduction of 'POULbella' by traditional budding was first done by L. Pernille and Mogens N. Olesen in their nursery in Fredensborg, Denmark in August 1990. This initial and other subsequent propagations conducted in controlled environments have demonstrated that the characteristics of 'POULbella' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, petals, floral parts, leaves, and stems of 'POULbella'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. New growth as well as a bare stem exhibiting thorns;

6. Leaves.

DETAILED DESCRIPTION OF THE VARIETY

The following is a description of 'POULbella', as observed in its outdoor growth in a field nursery in Jackson County, Oreg. Observations were conducted during August, 1998. Color references are made using The Royal Horticultural Society (London, England) Colour Chart, 1995, except where common terms of color are used.

For a comparison, several physical characteristics of the rose variety 'POULander', a red floribunda rose variety from the same inventors described and illustrated in U.S. Plant Pat. No. 6,265 and issued on Aug. 30, 1988 are compared to 'POULbella' in Chart 1.

CHART 1

| | 'POULbella' | 'POULander' |
|---|---|---|
| Flower bud, at ¼ open | Red Group 55A to 57B. | Red Group 46A to 46B. |
| Upper surface of petal on open bloom. | Red-Purple Group 57C. | Red Group 46B. |
| Petal count of flower. | 35–40 petals. | 20 petals. |
| Open flower, bloom size. | 50–80 mm. | 60–80 mm |

Parents:

*Seed parent.*—Unnamed, unpatented seedling.

*Pollen parent.*—Unnamed, unpatented seedling.

Classification:

*Botanical—Rosa hybrida.*

*Commercial.*—Floribunda.

FLOWER AND FLOWER BUD

Blooming habit: Continuous.

Flower bud:

*Size.*—Upon opening, 18 mm–22 mm in length from base of receptacle to end of bud.

*Bud form.*—Short, pointed.

*Bud color.*—As sepals unfold, Red Group 55A. Red Group 55A–55B at ¼ opening.

*Sepals.*—Green Group 144B when bud is cracking. As sepals open and fold back, approximately 50% show a basal color of Green Group 144B with shading of Greyed-Purple Group 185B. Strong foliaceous appendages on three of the five sepals. Surfaces of sepals moderately to strongly pubescent. Stipitate glands are present on the outer surface and the margins of the sepals. The stipitate glands have intonations of Greyed-Red Group 178A.

*Receptacle.*—Surface: Smooth. Shape: Funnel shaped. Size: Small, 6 mm (h)×4 mm (w). Color: Yellow-Green Group 144B.

*Peduncle.*—Surface: Limited numbers of stipitate glands. Length: 70–90 mm average length. Color: Yellow-Green Group 144B with some intonations of Greyed-Purple Group 183B present on 30–40% of the peduncles. Strength: Upright.

*Borne.*—Normally with multiple buds per stem. Range of 1 to 8 buds per flowering stem.

Flower bloom:

*Fragrance.*—Light, fruity scent.

*Duration.*—As a cut flower 3 to 5 days. The blooms have a duration on the plant of approximately 5 to 6 days. Petals fall cleanly away from plant.

*Size.*—Small to medium. Average flower diameter is 50–80 mm when fully open.

*Form.*—Informal, some flowers lightly quartered. Shape of flower when viewed from the side: Upon opening, upper part: Flattened convex. Upon opening, lower part: Flattened convex. Open flower, upper part: Flattened convex. Open flower, lower part: Concave.

*Petalage.*—Double. Average range: 35–40 petals per flower under normal conditions. Generally with 2–5 petaloids.

Color:

*Upon opening, petals.*—Outermost petals: Upper Surface: Red Group 55A. Reverse Side: Red-Purple Group 57D. Innermost petals: Upper Surface: Red-Purple Group 57B. Reverse Side: Red-Purple Group 57C.

*Upon opening, basal petal spots.*—Outermost petals: Outer Side: Green-White Group 157C. Inner Side: Green-White Group 157C. Innermost petals: Outer Side: White Group 155A. Inner Side: White Group 155A.

*After opening, petals.*—Outermost petals: Upper Surface: Red-Purple Group 57C. Reverse Side: Red-Purple Group 57D. Innermost petals: Upper Surface: Red-Purple Group 57C. Reverse Side: Red-Purple Group 57C.

*After opening, basal petal spots.*—Outermost petals: Outer Side: Green-White Group 157C. Inner Side: Green-White Group 157C. Innermost petals: Outer Side: White Group 155A. Inner Side: White Group 155A.

General tonality: On open flower, Red-Purple Group 57C. No change in the general tonality at the end of the fourth day. Afterwards, general tonality is Red-Purple Group 68D.

Petals:

*Petal reflex.*—Outer petals slightly reflexed. Many petals are slightly cupped.

*Petal edge.*—Generally smooth.

*Shape.*—Round.

*Petaloids.*—Present. Quantity: Few. 2–5 petaloids observed.

*Thickness.*—Thick.

*Arrangement.*—Informal.

Reproductive organs:

*Pollen.*—Color: Greyed-Yellow Group 161D. Abundance: Limited.

*Anthers.*—Size: Small. Color: Red Group 51D. Abundance: Average.

*Filaments.*—Color: Red Group 51A. Abundance: Average.

*Stigmas.*—Slightly inferior in location to anthers. Color: Greyed-Yellow Group 161A.

*Styles.*—Color: Yellow-Green Group 154D.

*Hips.*—None observed.

PLANT

Plant growth: Uniformly branched, vigorous, compact, and bushy. When grown as a budded field grown plant on *Rosa multiflora* understock, the average height of the plant itself is 120 cm and the average width is 100 cm.

Stems:

*Color.*—Young wood: Yellow-Green Group 144A. Older wood: Green Group 138A.

*Thorns.*—Incidence: Moderate. Size: Average length: 6 mm–8 mm. Color: Greyed-Orange Group 166C. Shape: Concave.

*Surface.*—Young wood: Smooth. Older wood: Smooth.

Plant foliage: Normal number of leaflets on normal leaves in middle of the stem: 5 leaflets. Leaflet configuration variable, many of the leaves exhibit incomplete leaflets growing from the stipule tips. Occasionally, leaflets are missing along the rachis.

*Leaf size.*—Medium. 95 mm (l)×75 mm (w).

*Abundance.*—Very abundant.

*Color.*—Upper Leaf Surface: Green Group 139A. Lower Leaf Surface: Green Group 137D. Juvenile foliage: Yellow-Green Group 146A. Anthocyanin intonations: Yes Location: On plants grown under high light conditions, juvenile leaflets and stems may exhibit strong intonations of Greyed-Red Group 184A.

Plant leaves and leaflets:

*Stipules*.—Size: 19 mm–22 mm. Color: Green Group 137C. On plants grown under high light conditions, juvenile penduncles may exhibit intonations of Greyed-Purple Group 184D. Presence of stipitate glands: Limited.

*Petiole*.—Length: Variable. 15 mm–25 mm. Color: Yellow-Green Group 144D with the center of the petiole sometimes exhibiting an intonation of Greyed-Purple Group 184D. Underneath: Generally smooth, with occasional prickles. Margins: Limited numbers of stipitate glands.

*Rachis*.—Color: Yellow-Green Group 144B. On plants grown under high light conditions, juvenile rachis may exhibit intonations of Greyed-Purple Group 184D. Underneath: Few to limited number of prickles. Margins: Very few.

*Leaflet*.—Edge: Finely serrated. Shape: Elliptic. Leaflet apex cuspidate in shape.

*Other*.—Moderately glossy to glossy. Thick.

Disease resistance: Excellent resistance to mildew, rust and *Botrytis* normal growing conditions in Jackson County, Oreg. The resistance to Black Spot in considered to be average to above average.

Winter hardiness: Winter hardy in Denmark and in Jackson County, Oreg.

We claim:

1. A new and distinct variety of rose plant of the floribunda class, substantially as herein illustrated and described as a distinct and novel rose variety due to its abundant, hot pink flowers, long period of bloom, vigorous growth, shiny dark green foliage, and disease resistance.

* * * * *

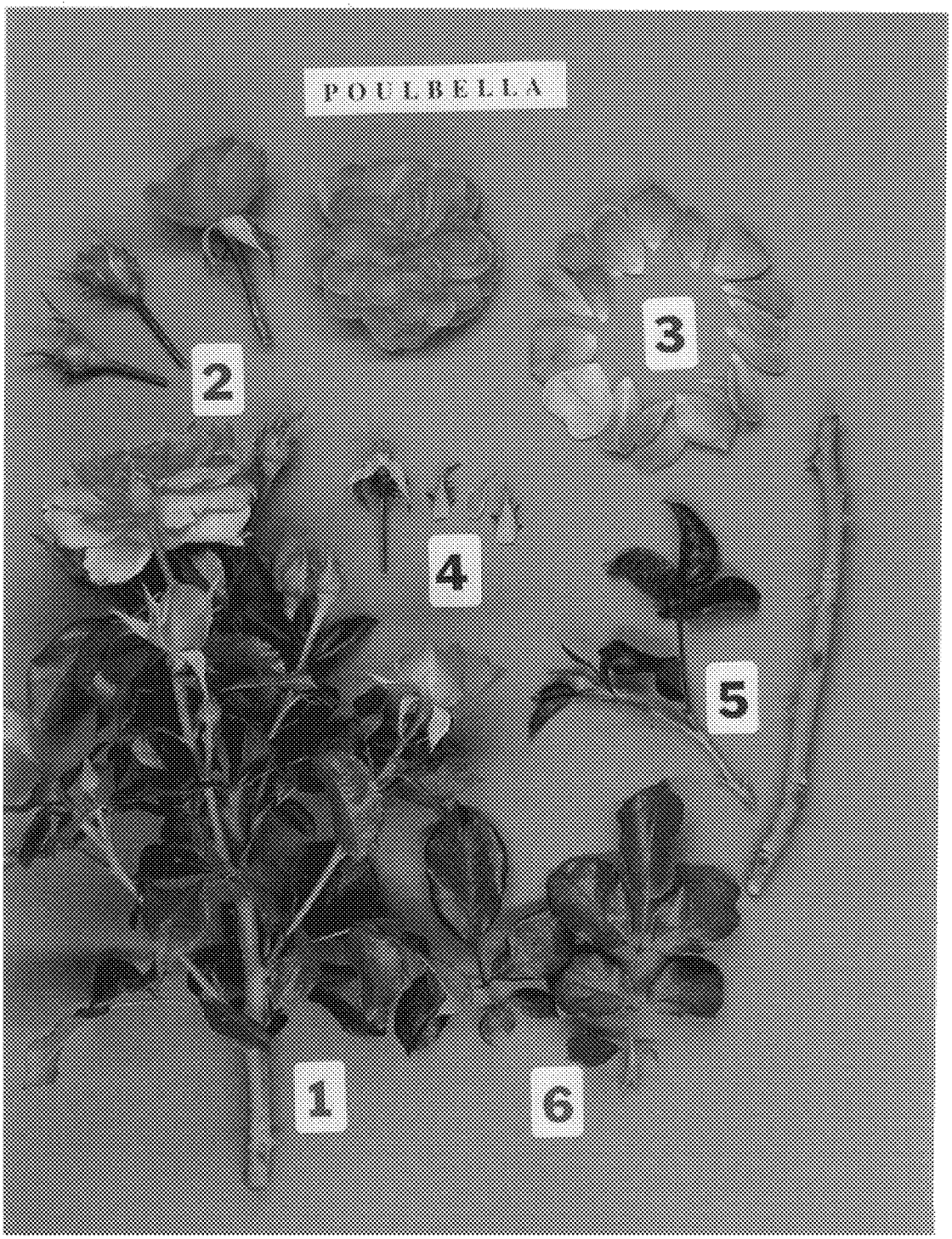
POULBELLA
2
3
4
5
1
6